US009510968B2

(12) United States Patent
Berry et al.

(10) Patent No.: US 9,510,968 B2
(45) Date of Patent: Dec. 6, 2016

(54) BACK BRACE WITH AUTOMATIC SENSING AND ADJUSTMENT

(71) Applicant: SpyneTech Inc., San Diego, CA (US)

(72) Inventors: Philip Berry, San Diego, CA (US); Caitlin Enomoto, San Diego, CA (US); Nicole Allen, New York, NY (US)

( * ) Notice: Subject to any disclaimer, the term of this patent is extended or adjusted under 35 U.S.C. 154(b) by 144 days.

(21) Appl. No.: 14/084,511

(22) Filed: Nov. 19, 2013

(65) Prior Publication Data

US 2014/0142485 A1 May 22, 2014

Related U.S. Application Data

(60) Provisional application No. 61/728,706, filed on Nov. 20, 2012.

(51) Int. Cl.
*A61F 5/02* (2006.01)
*G08B 21/04* (2006.01)
*A61B 5/11* (2006.01)
*A61B 5/00* (2006.01)

(52) U.S. Cl.
CPC ............. *A61F 5/028* (2013.01); *A61B 5/1116* (2013.01); *A61B 5/6812* (2013.01); *A61B 5/6823* (2013.01); *G08B 21/0446* (2013.01)

(58) Field of Classification Search
CPC .......... A61F 5/02; A61F 5/028; A61F 5/022; A61F 5/024; A61F 5/026; A61F 5/03; G08B 21/0446; A61B 5/11; A61B 5/1116; A61B 5/1117; A61B 5/6801; A61B 5/6804; A61B 5/6812; A61B 5/6823; A61B 5/6802; B25J 9/0006; A61H 1/02; A61H 2001/0203; A61H 3/008

USPC .......................................................... 602/19
See application file for complete search history.

(56) References Cited

U.S. PATENT DOCUMENTS

| | | | | |
|---|---|---|---|---|
| 2005/0043660 A1* | 2/2005 | Stark | ...................... | A61F 5/0106 602/19 |
| 2005/0279797 A1* | 12/2005 | Martin | ................. | A44B 11/065 224/637 |
| 2011/0082393 A1* | 4/2011 | Bort | ........................ | A61F 5/026 600/594 |
| 2013/0331755 A1* | 12/2013 | Rotblatt | .................... | A61F 5/00 602/19 |
| 2013/0345612 A1* | 12/2013 | Bannister | .............. | A61B 5/1116 602/19 |
| 2014/0024973 A1* | 1/2014 | Pettit | .................... | A61B 5/7275 600/595 |

* cited by examiner

*Primary Examiner* — Kari Petrik
(74) *Attorney, Agent, or Firm* — Kilpatrick Townsend & Stockton LLP

(57) ABSTRACT

An improved back brace apparatus employs sensors to automatically change the support provided to the back of a human torso. The sensors can detect the user changing position from a standing position to a bending position and the back brace apparatus automatically responds by increasing the support provided to the back of the user's torso. As the user returns to a standing position, the sensors detect the change and the back brace responds by automatically reducing the support provided to the back of the user's torso.

5 Claims, 14 Drawing Sheets

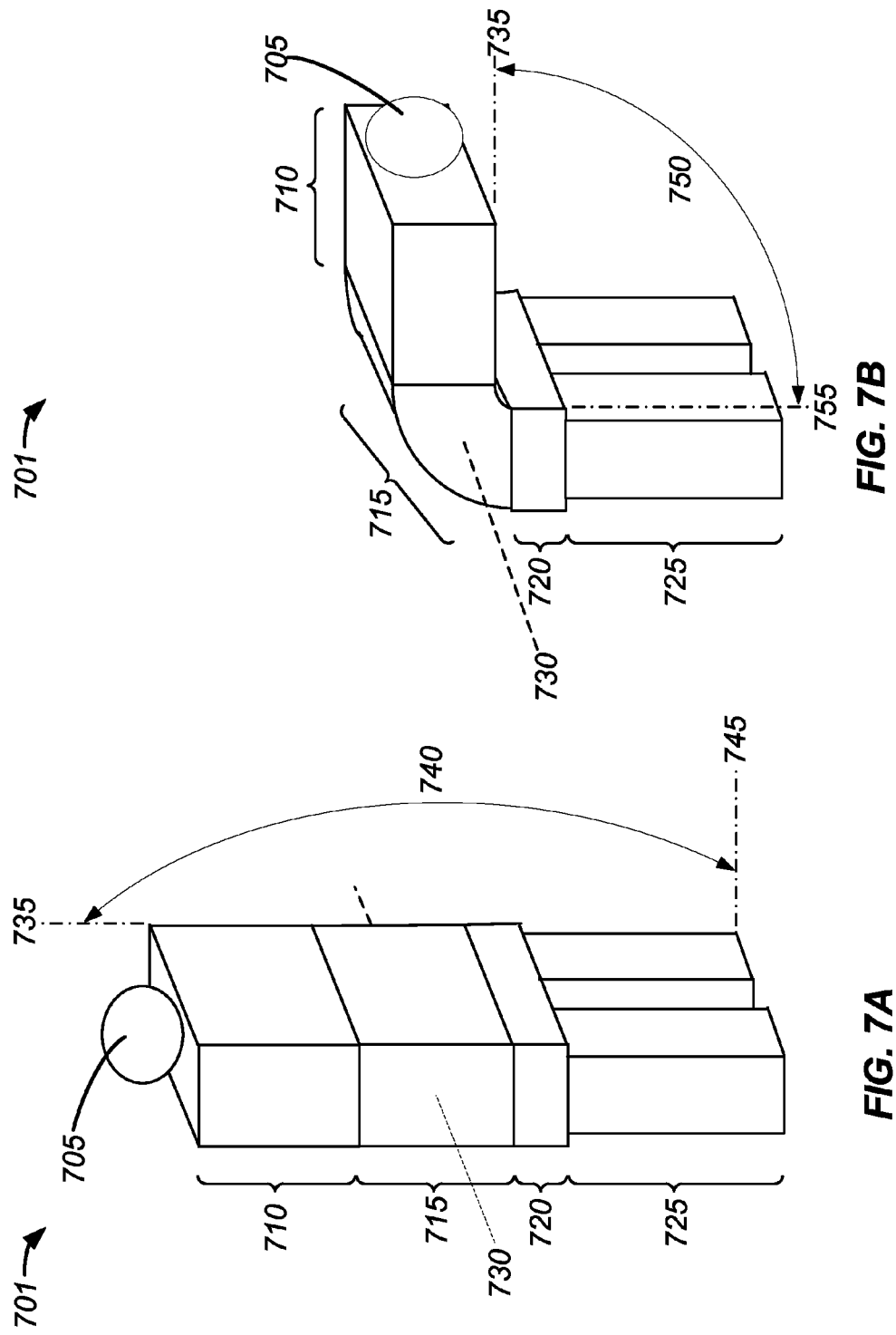

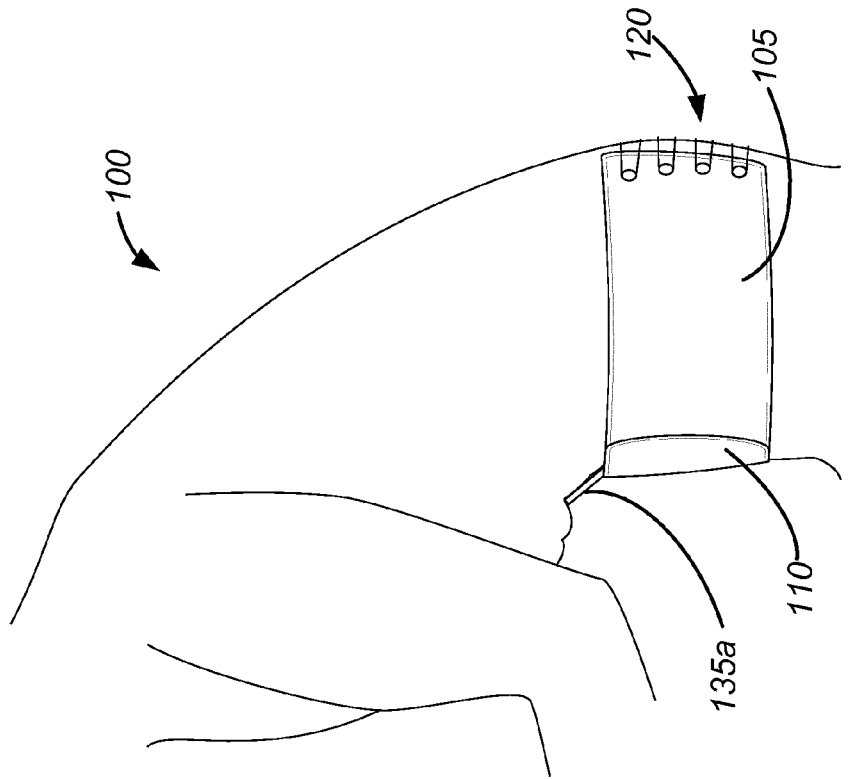
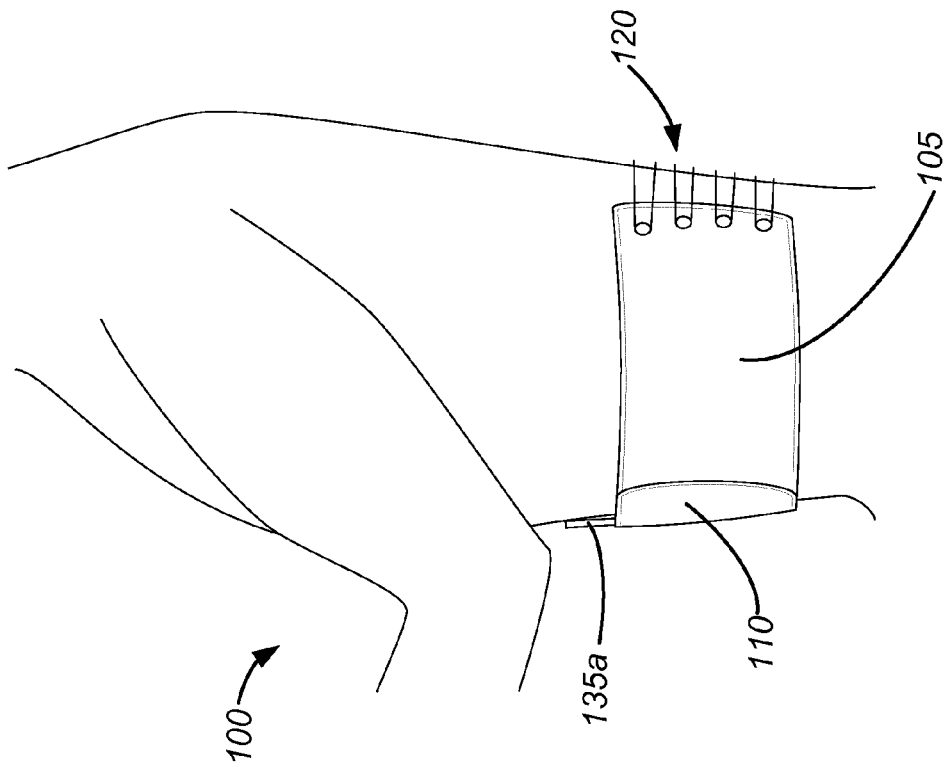

BACK BRACE WITH AUTOMATIC SENSING AND ADJUSTMENT

CROSS-REFERENCES TO RELATED APPLICATIONS

This application claims priority to Provisional Application No. 61/728,706 filed Nov. 20, 2012, titled "BACK BRACE WITH AUTOMATIC SENSING AND ADJUSTMENT", which is hereby incorporated by reference in its entirety.

BACKGROUND

The present invention relates generally to orthopedic devices for human use and, more particularly, back braces to assist persons with moving and lifting. During bending over or lifting, lower-back muscles contract to stabilize the lumbar spine. Some of these lower-back muscles are involuntary and they spring into action to protect the spine from lateral deformation and/or aid in moving one's torso. The back brace provides increased support for the user's lumbar spine when bending over or lifting to support the lower back muscles during such activity. Back braces are worn around the midsection of the user's torso and are manually adjusted by the user while standing to achieve the desired amount of support to the back portion of the user's torso.

As an example, back braces are sometimes used by laborers that have labor intensive jobs and perform heavy lifting as a routine activity. Laborers may adjust the back brace depending upon the task they are performing. For example, they may loosen the brace when standing and/or walking for less restriction and greater comfort, but may tighten the brace when they are preparing for bending over to perform heavy lifting. Back braces are also often used on medical patients as a recovery aid to protect their back muscles and promote a safe recovery following a surgical procedure or an injury. The user may adjust the back brace to wear it loosely when less support is needed and to wear it more tightly when more support is needed.

However, both the laborer and the medical patient may find it difficult and/or tedious to correctly adjust the brace every time they transition between needing less support and needing greater support. For example, the manual laborer may loosen the brace during a period of respite and forget to tighten it before lifting, or may tighten it inadequately when resuming lifting tasks. Further, the medical patient may require increased support while bending over and may forget to tighten the brace when transitioning from standing to bending. In some scenarios, patients may need to be continuously monitored on the job to determine the appropriate treatment for their back condition. These scenarios may result in back injury to the user and/or improper treatment.

Thus, it is desired that changes in looseness and tightness should be accommodated as users perform different activities. In addition, back monitors are needed that can continuously monitor a patient's torso while they perform everyday routines.

SUMMARY

Embodiments of the invention provide adjusting a back brace apparatus fitted to a human torso with detecting a change event of the human torso, and responding to the change event by controlling a back brace adjustment system to change a state of the back brace apparatus. The change event may comprise a change in position of the user and the apparatus may automatically adjust the support to a user's torso.

Some embodiments relate to back braces that employ one or more bending sensors to detect a change event of the user (e.g. bending or standing).

The sensors may communicate information regarding user's position to a controller, which may command a back brace adjustment system to change the state of the back brace apparatus. In some embodiments, the sensors may detect a bending event of the user and may increase the support provided to a back portion of the user's torso. In further embodiments, the sensors may detect a standing event of the user and decrease the support provided to a back portion of the user's torso.

Some embodiments may employ a back brace adjustment system comprising a mechanical adjustment system while other embodiments use a hydraulic or pneumatically actuated back brace adjustment system. One embodiment of a back brace adjustment system may comprise cables, pulleys and a tensioning motor. Other embodiments may employ a back brace adjustment system comprising bladders that may inflate, deflate and/or change rigidity, to change the state of the back brace apparatus.

Further embodiments may comprise a sensing apparatus and may not employ an adjustment apparatus. Such embodiments may be used to sense and record the motion of a user's torso for later use by a clinician, independently of an adjustment apparatus.

To better understand the nature and advantages of the present invention, reference should be made to the following description and the accompanying figures. It is to be understood, however, that each of the figures is provided for the purpose of illustration only and is not intended as a definition of the limits of the scope of the present invention.

BRIEF DESCRIPTION OF THE DRAWINGS

FIG. 7A is a diagram that illustrates a simplified perspective view of a human wearing the back brace illustrated in FIG. 1.

FIG. 7B is a diagram that illustrates a simplified perspective view of a human wearing the back brace illustrated in FIG. 1.

FIG. 8A is a diagram that illustrates a side view of a user wearing a back brace apparatus, in accordance with an embodiment of the invention.

FIG. 8B is a diagram that illustrates a side view of a user wearing a back brace apparatus, in accordance with an embodiment of the invention.

DETAILED DESCRIPTION

Figure 1:
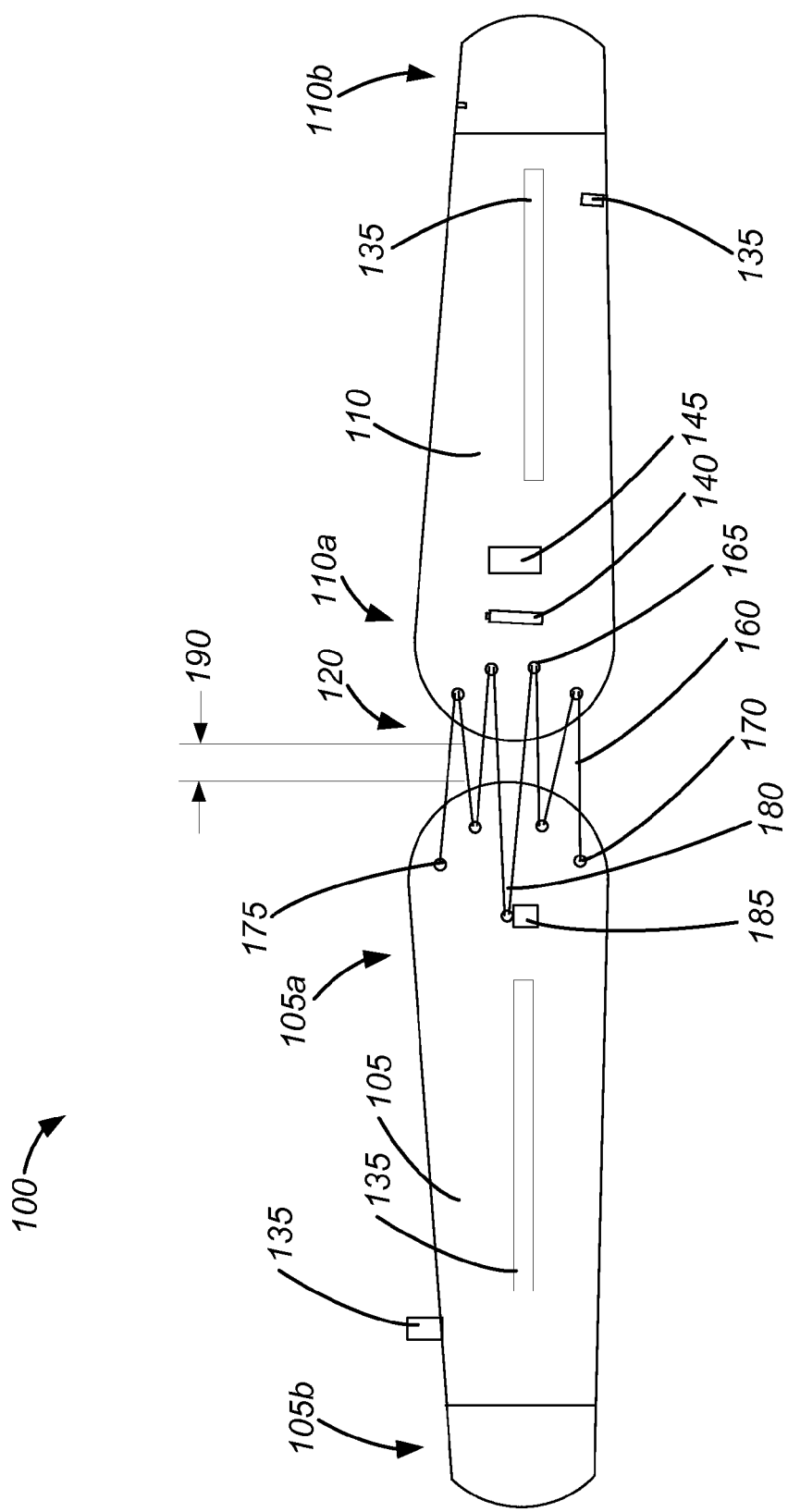
FIG. 1 is a view of a back brace apparatus constructed in accordance with an embodiment of the invention in an orientation ready to be worn around the torso of a user.

FIG. 1 illustrates one embodiment of a back brace apparatus 100 for use on a user's torso. A back brace adjustment system 120, which will be described in more detail below, may be used to increase or decrease the support to a back portion of the user's torso. In some embodiments, the back brace apparatus 100 may comprise multiple segments, while in other embodiments back brace apparatus 100 may comprise a single elongated belt segment. FIG. 1 shows an embodiment with multiple segments, comprising a first elongated belt segment 105 and a second elongated belt segment 110. First belt segment 105 may have an adjusting end 105a attached to a back brace adjustment system 120, and a fastening end 105b. Similarly, second belt segment 110 may have an adjusting end 110a attached to back brace adjustment system 120, and a fastening end 110b. The back brace apparatus 100 may further be equipped with one or more user bending sensors 135, a controller 145, and a battery 140, each of which will be described in more detail below.

In further embodiments the back brace apparatus 100 may comprise a single belt segment with the back brace adjustment system 120 attached to it and configured to operate similar to embodiments with two belt segments. In some embodiments the single belt segment may have a flexible portion that may accommodate a decrease in belt circumference proximate the back brace adjustment system 120.

Figure 2:
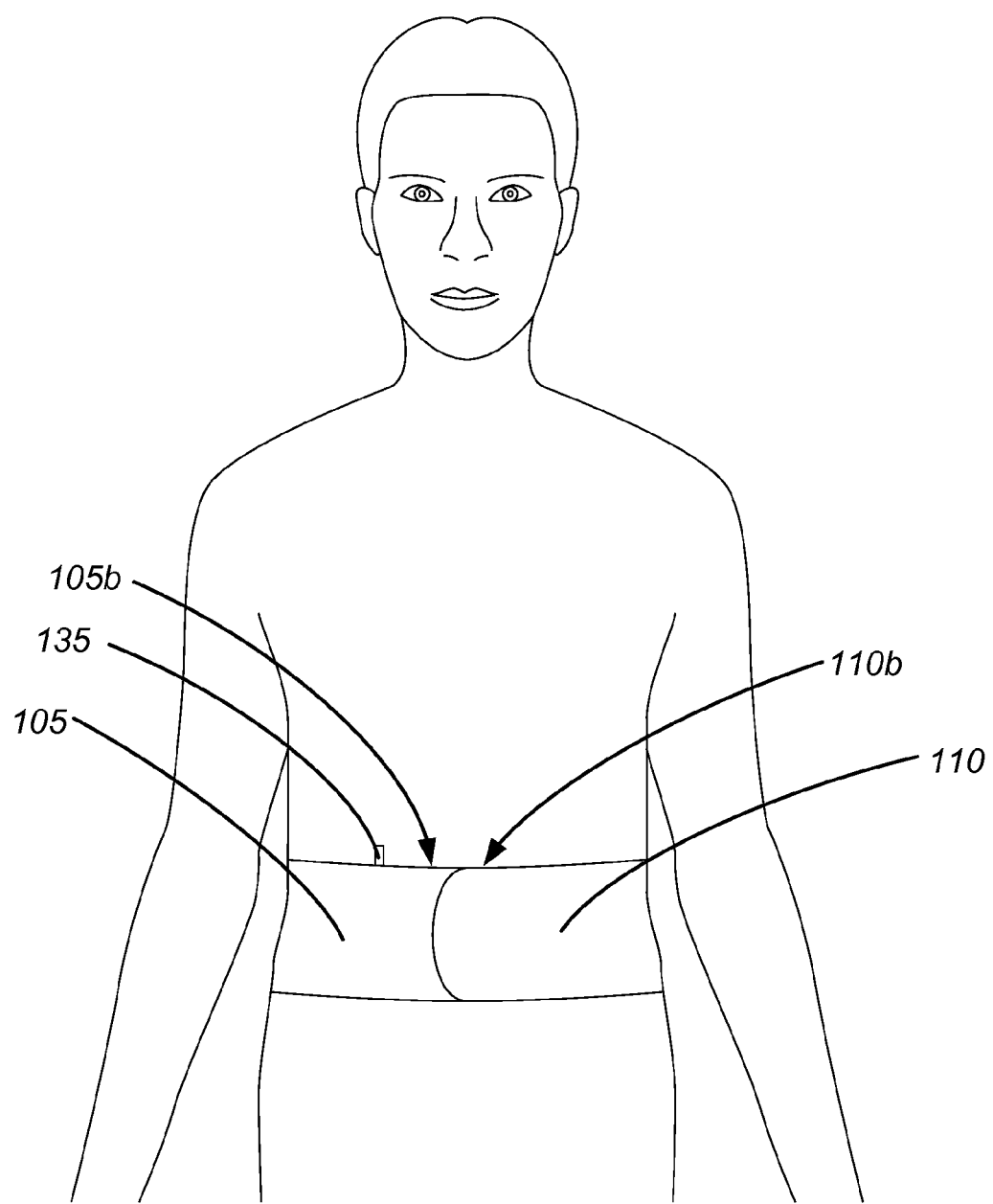
FIG. 2 is a diagram that illustrates a front view of a user wearing the back brace apparatus illustrated in FIG. 1.
Figure 3:
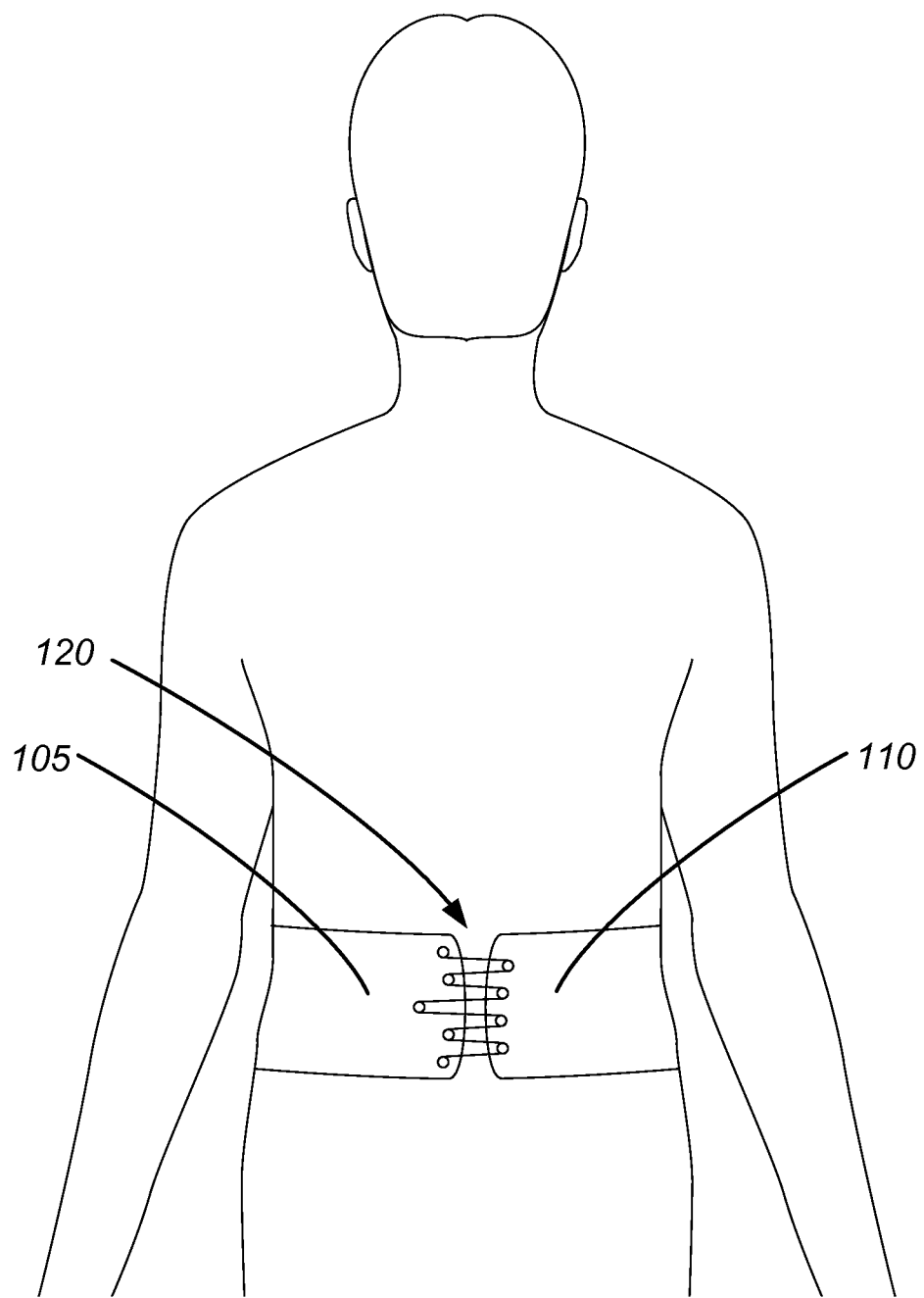
FIG. 3 is a diagram that illustrates a rear view of a user wearing the back brace apparatus illustrated in FIG. 1.

A user may fit the back brace apparatus 100 around their torso as approximately illustrated in FIG. 2. As shown, the fastening ends 105b, 110b of the belt segments 105, 110 may be fastened together at the front of the user. In some embodiments, fastening the two segments may be accomplished, for example, with hook and loop material, a buckle, or a latch. In further embodiments, the fastening ends 105b, 110b may be aligned with the front of the user to facilitate ease of securing the belt by the user. As illustrated in FIG. 3, in some embodiments the back brace adjustment system 120 may be positioned approximately adjacent the spine of the user.

Figure 4:
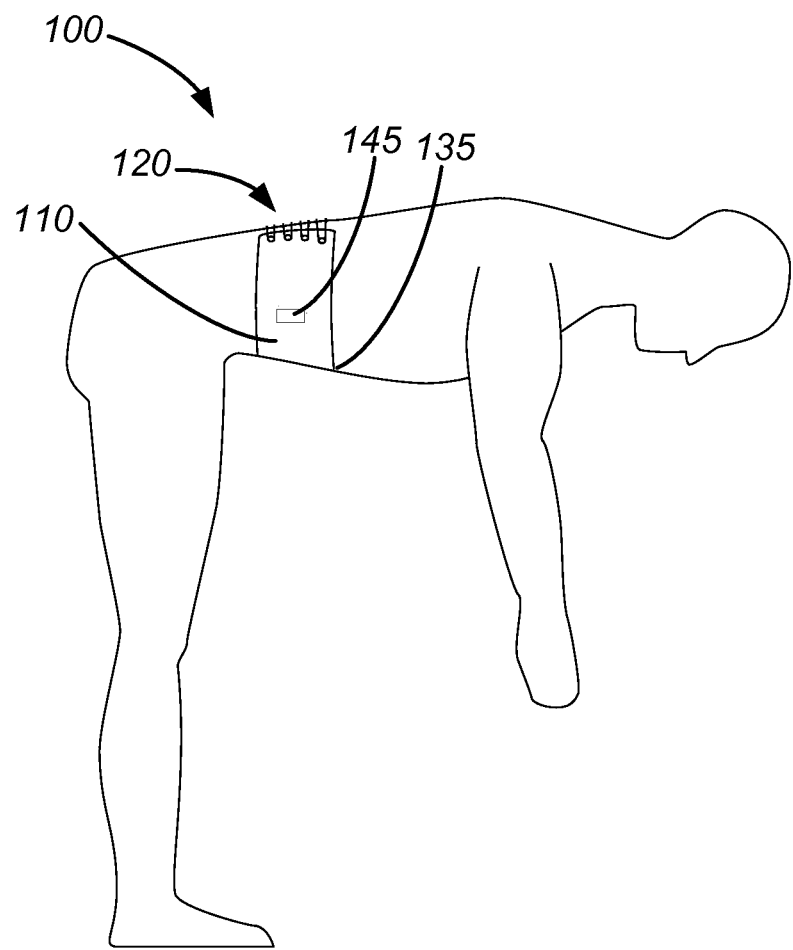
FIG. 4 is a diagram that illustrates a side view of a user wearing a back brace apparatus illustrated in FIG. 1.

When the user bends over, as illustrated in FIG. 4, the one or more user bending sensors 135 may detect the bending over as a change event of the torso and send a notification signal to the controller 145. The controller 145 may receive the notification signal and then control the back brace adjustment system 120 to change the state of the back brace apparatus 100 in response. In some embodiments the sensors may be affixed to the back brace apparatus and be configured to detect the angle of an upper portion of the torso relative to a lower portion of the torso. Such sensors may comprise a strain gauge positioned proximate the front of the user's torso. In other embodiments the sensors may be affixed to the upper portion of the user's torso and be configured to detect the angle of the upper portion of the torso relative to a ground surface. Such sensors may use acceleration, gravitational forces or other means to detect the position of the upper portion of the torso.

For example, in some embodiments, when the bending sensors 135 detect a user bending event, the controller 145 commands the back brace adjustment system 120 to become more stiff, or to tighten, and provide increased support to a back portion of the user's torso. More specifically, the back brace apparatus 100 may change state to aid the lower back muscles of the user, and to stabilize the lumbar spine from lateral deformation. In one embodiment, changing the state of the back brace may comprise inflating one or more bladders on the front, back or side of the user for example when the user needs to be supported differently on either side. Further, when the user stands up, the bending sensors 135 may detect a standing event and notify the controller 145 to make the back brace adjustment system 120 loosen/relax the brace, providing decreased support to a back portion or side portion of the user's torso. The various embodiments and functions of the one or more bending sensors 135 will be discussed in more detail below. The position of the back brace apparatus on the human torso in FIG. 4 may not be representative of the location of the back brace apparatus in other embodiments.

Myriad back brace adjustment systems 120 may be employed to change the state of the back brace apparatus 100. Referring back to the embodiment illustrated in FIG. 1, the apparatus employs a serpentine cable 160 fitted around a plurality of pulleys 165 disposed on the adjustment ends 105a, 110a of both belt segments 105, 110. The serpentine cable 160 may have two fixed ends 170, 175 attached to the belt segment 105 and a tensioned segment 180, coupled to a tensioning device 185. As mentioned above, some embodiments may employ a belt with a single belt segment. In some embodiments, the tensioning device 185 may be a motor coupled to a spool that may be controlled by the controller 145. When the spool rotates in one direction, the tensioned segment 180 of the cable 160 may be pulled tighter, decreasing the space 190 between the belt segments 105, 110, or reducing the circumference of embodiments having only a single belt segment. When the tensioned segment 180 of the cable is pulled tighter, the state of the back brace apparatus 100 is changed from lesser tension and support to greater tension and support to a back portion of the user's torso. Conversely, when the motor rotates the spool in the opposite direction, the tensioned segment 180 of the cable 160 may be loosened, increasing the space 190 between the belt segments 105, 110. This may change the state of the back brace apparatus 100 from greater tension to lesser tension, providing decreased support to a back portion of the user's torso.

Figure 5:
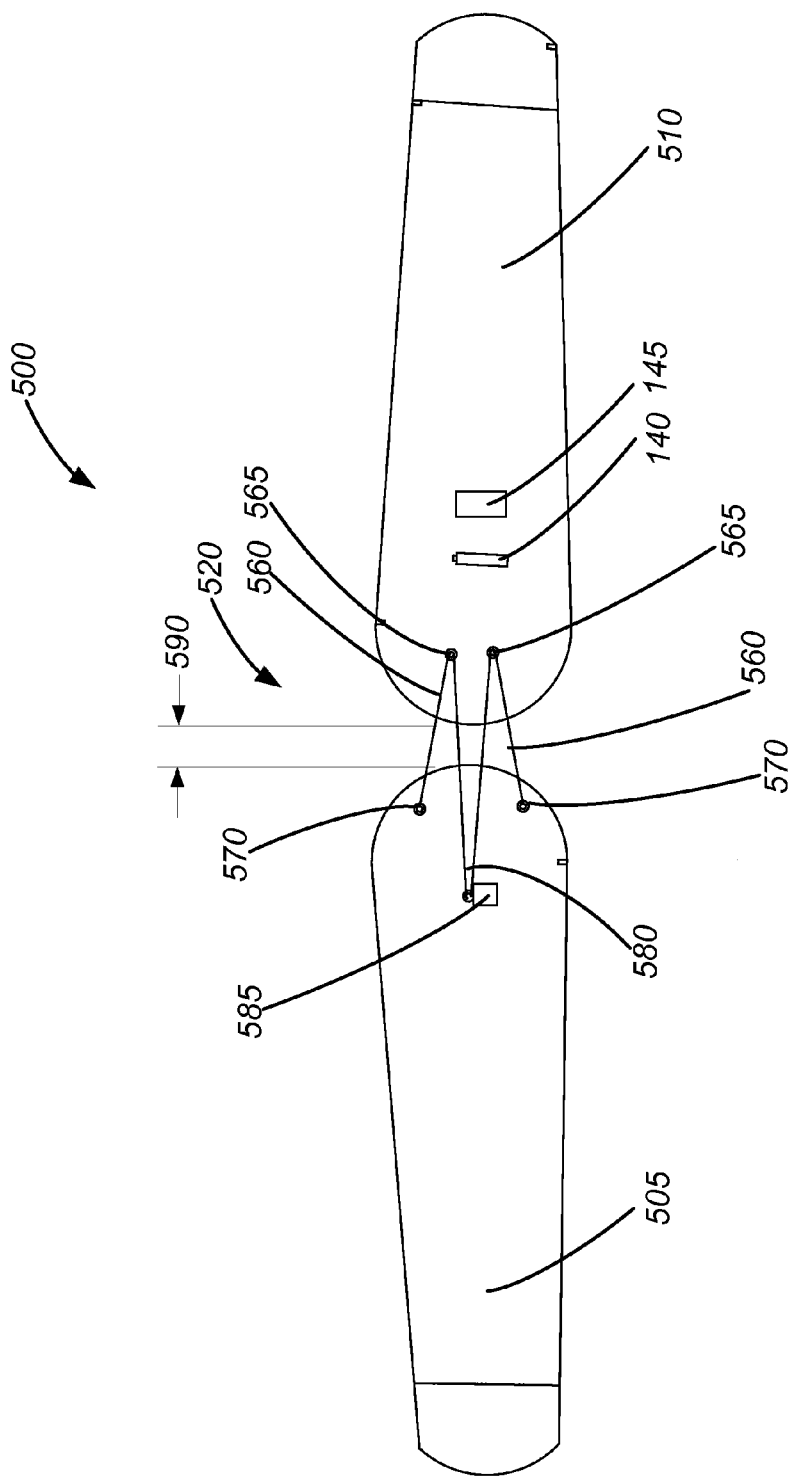
FIG. 5 is a diagram that illustrates a plan view of a back brace apparatus illustrated in FIG. 1.

FIG. 5 shows another embodiment of a back brace adjustment system 520. In this embodiment, a pair of cables 560 both have fixed ends 570 and tensioned ends 580 located on a first belt segment 505. On a second belt segment 510, the cables 560 may be looped around a pair of pulleys 565. The tensioned end 580 of the cables 560 may be coupled to a tensioning device 585. In some embodiments, the tensioning device 585 may be a motor coupled to a spool that may be controlled by the controller 145 to rotate wherein, in one direction of rotation, the tensioned segment 580 of the cables 560 may be pulled tighter, decreasing the space 590 between the belt segments 505, 510. This may change the state of the back brace apparatus 500, providing increased support to a back portion of the user's torso. Conversely, when the motor rotates the spool in the opposite direction, the tensioned segment 580 of the cables 560 may be loosened, increasing the space 590 between the belt segments 505, 510. This may change the state of the back brace apparatus 500, providing decreased support to a back portion of the user's torso.

Figure 6:
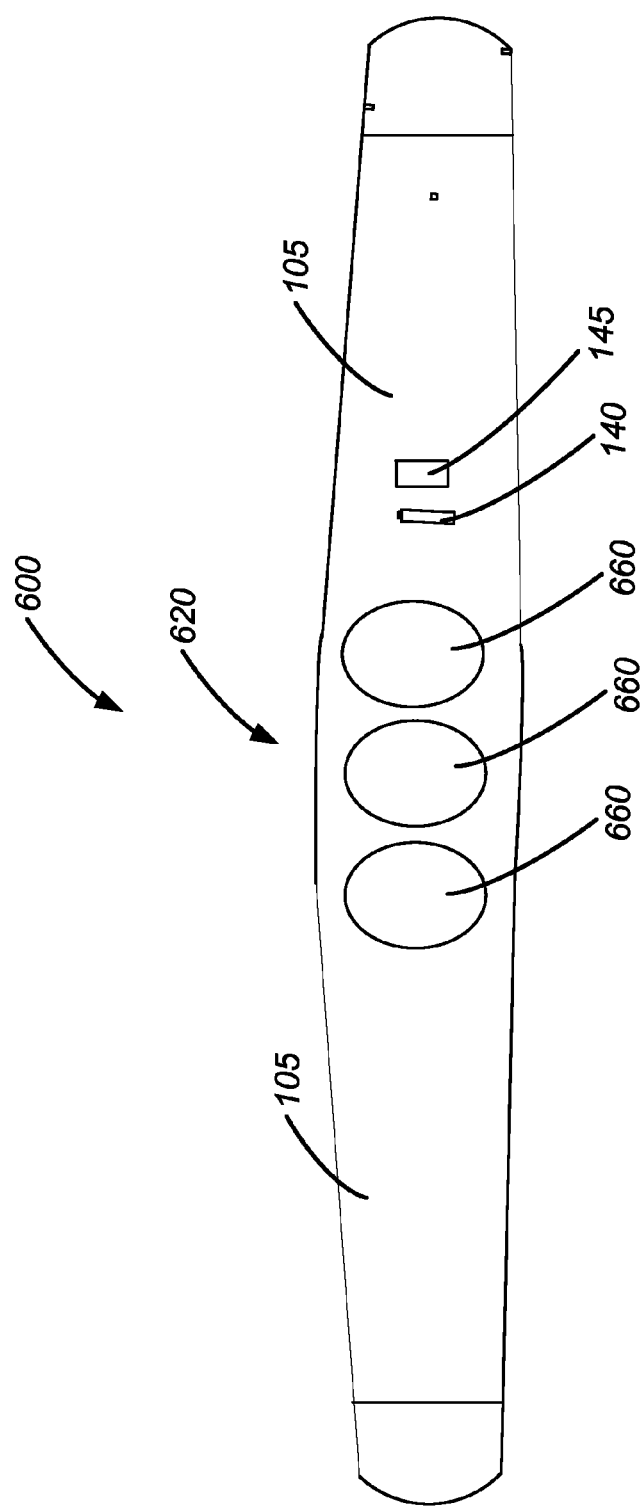
FIG. 6 is a diagram that illustrates a plan view of a back brace apparatus illustrated in FIG. 1.

A further embodiment of a back brace adjustment system 620 is illustrated in FIG. 6 and provides a hydraulic or pneumatic actuation adjustment, rather than the mechanical adjustment described thus far. In this embodiment, one or more bladders 660 may be positioned on the back and/or side portions of the back brace apparatus 600. In some embodiments, as illustrated here, the back brace apparatus 600 may comprise only a single belt segment 105. In the FIG. 6 embodiment, the bladders 660 may be pneumatically actuated and coupled to an air supply system (not shown) capable of inflating and deflating the bladders to change the state of the back brace apparatus 600 between increased support to a back portion of the user's torso and decreased support. For example, the back brace adjustment system 620 may employ an air pump, a compressed gas cylinder and valve, or another means of inflation and deflation. Alternatively, the back brace adjustment system 620 may employ a valve mechanism to fill and empty the bladders with a working fluid, such as relatively incompressible fluid or oil or water or the like. The controller 145 may control the air pump or the valve, or both, to allow air or the working fluid to enter the bladders 660, inflating them. This may result in a change in state of the back brace apparatus 600, providing increased support to a back portion of the human torso. Similarly, the controller 145 may control the air pump or valve, or both, to deflate the bladders 660, which may decrease the support to a back portion of a human torso. In some embodiments the bladders may be individually controlled so support may be selectively provided to the back or sides of the human torso.

FIG. 6 shows in a similar embodiment, in which, instead of the back brace adjustment system 620 comprising bladders 660 filled with air, the bladders may be filled with a working fluid such as a magnetorheological fluid. The magnetorheological fluid comprises a smart fluid suspended in a carrier fluid, usually a type of oil. When subjected to a magnetic field, the magnetorheological fluid greatly increases its apparent viscosity, to the point of becoming a viscoelastic solid. Typically, an electromagnet is used to activate the fluid. When in its active ("on") state, the yield stress of the fluid can be controlled very accurately by varying the magnetic field intensity of the electromagnet. Thus, when the electromagnet of the back brace adjustment system 620 is activated by the controller 145, the state of the back brace apparatus 600 may change, increasing the rigidity of the bladders 660 and providing increased support to a back portion of a human torso. Conversely, when the electromagnet is deactivated by the controller 145 the state of the back brace apparatus 600 may change, decreasing the rigidity of the bladders 660 and providing decreased support to a back portion of a human torso.

The above description of various back brace adjustment systems is for example only and other embodiments may employ other back brace adjustment systems without departing from the invention. For example, as illustrated in FIG. 6, the bladders may be filled with water or another fluid to change the state of the back brace apparatus between increased support and decreased support. Further embodiments may employ a piezoelectric panel in the back brace adjustment system such that when activated the panel may become rigid, changing the state of the back brace apparatus between increased support and decreased support. Other embodiments may employ a combination of adjustment systems such as, for example, bladders on either side of the user's torso and a serpentine adjustment cable in the back. Additional embodiments may employ other methods to change the state of the back brace apparatus.

FIGS. 7A and 7B illustrate a simplified human body 701, and will be used to show the location of the back brace apparatus 100 (see FIG. 1) on the user employed in some embodiments, as well as the various embodiments of the one or more bending sensors 135. FIG. 7A shows a simplified human 701 in a standing position. The simplified human has a head 705, an upper portion of a torso 710, a bending portion of a torso 715 and a lower portion of a torso 720. Thus, in the standing position, the human torso may comprise an upper portion 710 that may be approximately vertically aligned with a bending portion 715 that may be approximately vertically aligned with a lower portion 720. Legs 725 are attached to the lower portion of the torso.

FIG. 7B shows the simplified human body in a bending position. In the bending position, the upper portion 710 of the torso may be in a near horizontal position, the bending portion 715 may be arcuate in shape, and the lower portion 720 may remain substantially vertically oriented. The change event of the human body 701 between a standing position and a bending position may be more clearly described by locating an axis of bending 730 in the approximate center of the bending portion 715 of the human torso. Further, angular references about axis 730, with regard to the top portion 710 of the human torso may be employed. For example, in FIG. 7A, an angle 740 represents the angle of the top portion 710 of the human torso relative to a horizontal ground surface 745. In FIG. 7B, an angle 750 represents the angle of the top portion 710 of the human torso relative to the position of the lower portion 720 of the human torso. These two angles 740, 750 may be used to determine the position of the upper portion of the torso relative to the lower portion of the torso, about the bending axis 730. In some embodiments, more complex bending and twisting of the upper portion of the torso relative to the lower portion of the torso may occur. Such complex bending of the torso is within the consideration and scope of the invention.

Thus, two general types of bending sensors that may be employed in the embodiments are described. A first type of bending sensor may be used to detect "deflection" of the belt or of a portion of the user. Deflection sensors may be used to detect an angle 750, which is the angle of the top portion 710 of the human torso relative to the position of the lower portion 720 of the human torso. These "deflection" bending sensors are typically affixed to one of the belt segments and may be positioned to detect changes in position, strain or pressure. In some embodiments deflection sensors may also be used to determine a change in length of the belt. In some embodiments such sensors may be strain gauges. A strain gauge is a device used to measure strain on an object. In some embodiments, the strain gauge consists of an insulating flexible backing which supports a metallic foil pattern. The strain gauge is attached to a deformable object. As the object is deformed, the foil is deformed, causing its electrical resistance to change. This resistance change, usually measured using a Wheatstone bridge, is related to the strain experienced by the object, by the quantity known as the gauge factor.

The second type of bending sensor that may be employed in some embodiments is a "position" sensor that may be used to detect a change in position of the user with respect to ground, or one portion of the user relative to another portion. In some embodiments, the position sensor may be used to detect an angle 740 that is the angle of the top portion 710 of the human torso relative to a horizontal ground surface 745. These sensors may typically be affixed to the top portion 710 of the torso or to the back brace apparatus 100 and detect the change in position or angle of the user. These bending "position" sensors can typically detect changes in angle, position, and/or alignment with each other or with respect to a reference such as a ground surface 745, as described in more detail below. They can also detect changes in position of one portion of the user's body with respect to another portion. In some embodiments, position sensors may be used on the belt and on the upper portion of the torso so that all bending, twisting and relative motion between the user's lower portion of the torso and the upper portion of the torso may be determined, including more complex twisting of the torso.

In some embodiments, the "position" sensors may be implemented with what is known in the art as an inertial measurement unit (IMU). An IMU is an electronic device that measures and reports on a body's velocity, orientation, and gravitational forces, using a combination of accelerometers and gyroscopes, sometimes also magnetometers. An IMU works by detecting the current rate of acceleration using one or more accelerometers, and detects changes in rotational attributes like pitch, roll and yaw using one or more gyroscopes. Some IMU's also include a magnetometer, mostly to assist calibrate against orientation drift. Angular accelerometers measure how the body is rotating in space. Generally, there is at least one sensor for each of the three axes: pitch (nose up and down), yaw (nose left and right) and roll (clockwise or counter-clockwise). Linear accelerometers measure non-gravitational accelerations of the body. Since it can move in three axes (up & down, left & right, forward & back), there is a linear accelerometer for each axis.

In a configured back brace apparatus such as described herein, A computer continually calculates the body's current position. First, for each of the six degrees of freedom (x,y,z and θx, θy and θz), it integrates over time the sensed acceleration, together with an estimate of gravity, to calculate the current velocity. Then it integrates the velocity to calculate the current position. In some embodiments the sensors are used in conjunction with each other to determine the change in position or orientation of one or more sensors relative to one or more other sensors. In some embodiments, this provides the ability to determine the movement of one portion of the user's body relative to other portions of the user's body. For example, in one embodiment, one or more IMU's may be attached to the belt and one or more IMU's may be attached to the user's upper torso. Computations may be performed to determine the change in position of the user's torso relative to the sensors on the belt, detecting bending, twisting and deflection of the upper torso relative to the lower torso. Such sensors may also be used to null out movements of the entire body such as rotating in a rotatable chair.

In some embodiments, the back brace apparatus 100 (see FIG. 1) may be fitted upon bending portion 715 of the human torso. In further embodiments the preferred location of the back brace apparatus 100 may be proximate the L4 and L5 vertebrate. As illustrated in FIG. 1, in some embodiments one or more of the bending sensors 135 may be secured to either one or both of the belt segments 105, 110 of the back brace apparatus 100.

One embodiment of a bending sensor 135a is depicted in FIGS. 8A and 8B. The bending sensor 135a may comprise an elongated tab disposed in the front portion of one of the belt segments 105, 110. The bending sensor 135a may be employed to sense the bending of a user's torso. For example, as illustrated in FIG. 8A, the elongated tab may be approximately vertically aligned with the user's front torso, or stomach, when the user is in a standing position. As illustrated in FIG. 8B, when the user bends over, a portion of the user's stomach may push on the elongated tab, causing it to deflect. The deflection causes the sensor to indicate user bending, such as by changing an electrical property of the sensor or changing an output of the sensor. More specifically, when transitioning from a standing position to a bending position (a change event of the human torso) the elongated tab may be positioned on the belt 105, 110 and configured to bend, providing input regarding the angle 750 (see FIG. 7B) to the controller 145 (see FIG. 1). Myriad technologies may be employed in the bending sensor 135a to electronically sense the deflection of the elongated tab including, for example, a strain gauge or a piezoelectric sensor.

Figure 8D:
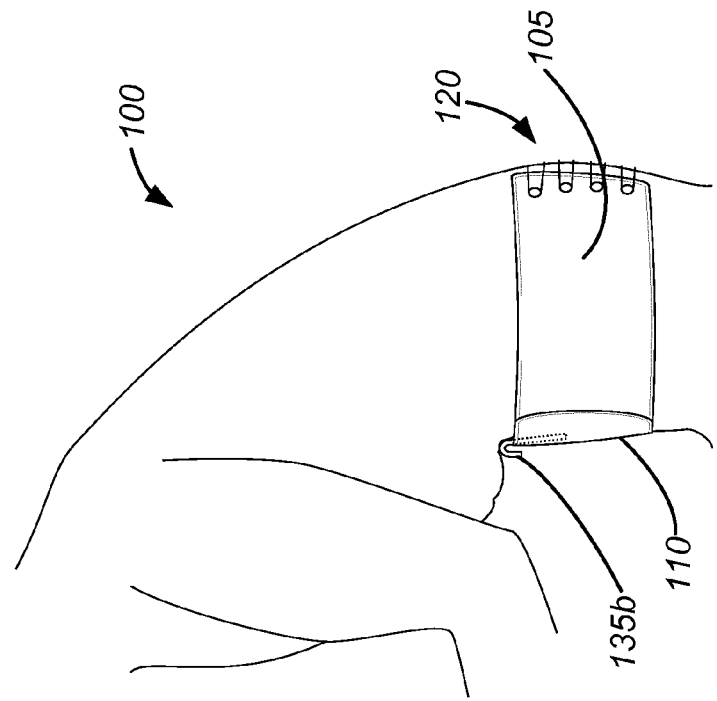
FIG. 8D is a diagram that illustrates a side view of a user wearing a back brace apparatus, in accordance with an embodiment of the invention.
Figure 8C:
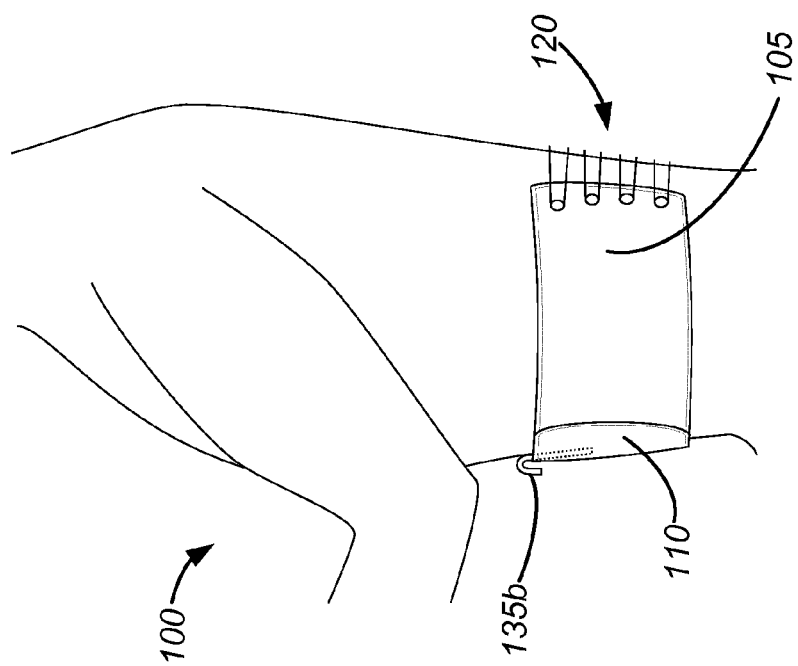
FIG. 8C is a diagram that illustrates a side view of a user wearing a back brace apparatus, in accordance with an embodiment of the invention.

Another embodiment of a bending sensor 135b is depicted in FIGS. 8C and 8D. The bending sensor 135b may comprise a tab formed in a "U" shape and disposed in the front portion of one of the belt segments 105, 110. The bending sensor 135b may sense the bending of a user's torso. For example, as illustrated in FIG. 8C, the stomach may have little or no contact with the "U" shaped tab when the user is in a standing position. As illustrated in FIG. 8D, when the user changes position to a bending position, a portion of the user's stomach may push on the "U" shaped tab causing it to deflect. More specifically, when transitioning from a standing position to a bending position the "U" shaped tab may be positioned to bend relative to the torso, providing input regarding the angle 750 (see FIG. 7B) to the controller 145 (see FIG. 1). Myriad technologies may be employed to electronically sense the deflection of the "U" shaped tab including, for example, a strain gauge or a piezoelectric sensor. Such sensors may be used on any portion of the back brace apparatus to detect bending or twisting of the torso.

The bending sensors 135a, 135b may be able to sense the full range of motion of the user's torso from a standing position to a bending position and provide continuously variable input to the controller 145. In some embodiments this may enable the back brace apparatus 100 to be adjusted at the appropriate point in the transition between user positions so the user does not suffer back injury. In further embodiments, more than one sensor may be used and/or the bending sensors 135 may be located on a different portion of the belt segments 105, 110, as described in more detail below. In further embodiments, myriad numbers, positions and configurations of the bending sensors 135 may be used.

In other embodiments, one or more bending sensors 135 may detect the angle 740 (see FIG. 7A), which is the angle of the top portion 710 of the human torso relative to a horizontal ground surface 745. For example, an IMU, gyroscopic, gravitational or accelerometer type sensor may be employed on the upper portion 710 (see FIG. 7A) of the human torso or in the belt segments 105, 110 to indicate the sensor's angle with respect to the ground surface 745. For example a gravitational sensor may be configured to determine its orientation relative to the ground surface 745 and attached to the upper portion 710 (see FIG. 7A) of the human torso. Thus, when the upper portion 710 (see FIG. 7A) of the human torso is in a standing position (see FIG. 7A), the angle 740 is approximately 90 degrees. However, when in the bending position (see FIG. 7B), the angle 740 is approximately 0 degrees. A gyroscopic and/or an accelerometer sensor may work similarly, and once calibrated, it may indicate the relative change in orientation of the upper portion 710 (see FIG. 7B) of the human torso relative to the ground surface 745, enabling the controller 145 (see FIG. 1) to detect a bending or a standing event (change in position of the human torso).

Figure 8E:
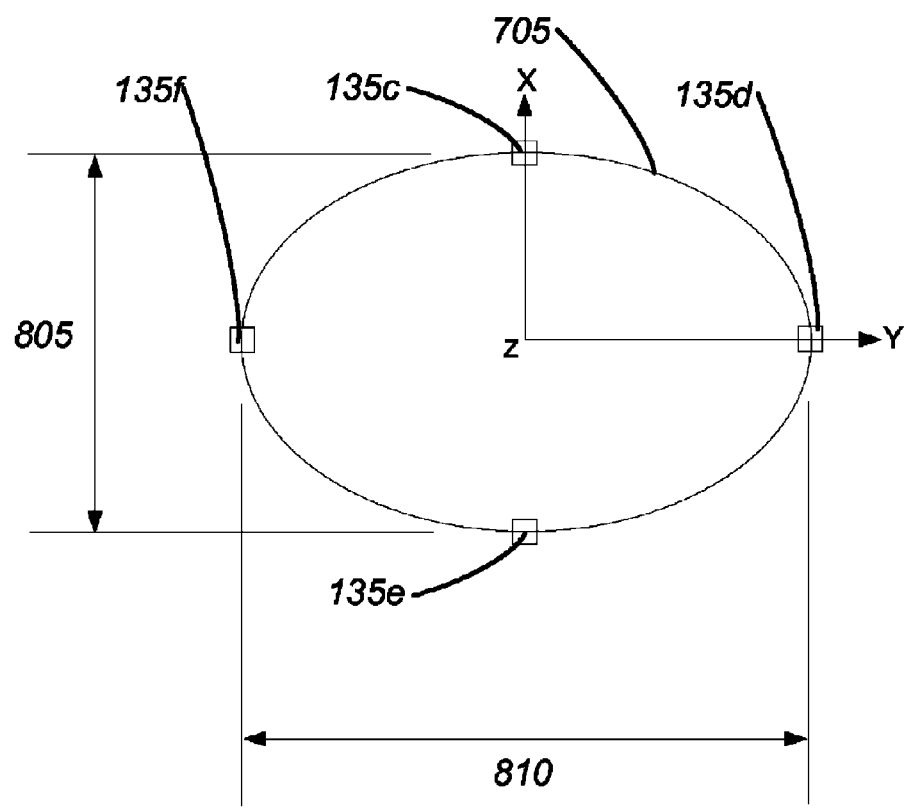
FIG. 8E is a diagram that illustrates sensors located on X, Y, Z axial coordinates, in accordance with an embodiment of the invention.

In one embodiment, illustrated in FIG. 8E, there may be four bending sensors 135c-135f that are in communication with one another and may detect relative motion. The sensors 135c-135f may be located on X, Y, Z axial coordinates as illustrated. In some embodiments an additional sensor may be located on upper portion of the torso 710. Multiple sensors may be employed in combination with each other to sense bending, twisting and other motion of the upper torso 710 with respect to the lower torso 720. To improve the accuracy of sensors 135c-135f, in some embodiments the torso thickness 805 and torso width 810 may be known so that the relative position of each sensor 135c-135f may be determined. In further embodiments a belt length sensor may be used to determine the length of the back brace apparatus around the torso so the sensor location may be more accurately determined. In some embodiments the belt length sensor may include an electro-resistive stretchable material that changes resistance when stretched. In one embodiment the stretchable material is a conductive rubber cord. In further embodiments the cord may be approximately two millimeters in diameter and made of carbon-black impregnated rubber. In a 'relaxed' state, the resistance may be relatively low, however as it is stretched the resistance may increase as the conductive particles in the rubber get further apart.

Bending sensors 135 may be employed by themselves, or in conjunction with each other and/or other sensors to sense a change event of the human torso. For example, one or more IMU's may be placed on the front portion of the belt segments 105, 110 (see FIG. 1) and one or more IMU's may be placed on the back portion of the belt segments. An algorithm may be developed for use in the controller 145 (see FIG. 1) to employ input from all the bending sensors 135 to sense a change event of the human torso.

In further embodiments, one or more bending sensors 135 (see FIG. 1) may comprise pressure sensors that may be integrated into one or more belt segments 105, 110. The pressure sensors may sense the pressure applied by the bending portion 715 (see FIG. 7A) of the human torso to the belt segments 105, 110 (see FIG. 1), and provide input to the controller 145 to aid in the detection of a change event of the human torso. For example, when transitioning from a standing position to a bending position, the relative pressures on the pressure sensors may change, providing input to the controller 145 (see FIG. 1) that a change event has occurred. Pressure sensors are well known in the art and myriad different pressure sensing technologies may be employed, for example, strain gauge or piezoelectric technologies.

In another embodiment, a potentiometer may be employed to detect the angle 750 (see FIG. 7B), which is the angle of the top portion 710 of the human torso relative to the position of the lower portion 720 of the human torso. A potentiometer may be configured to have two portions that move relative to each other with a sensing apparatus disposed at the intersection of the two portions. Thus when one portion moves relative to the other portion the controller 145 (see FIG. 1) can determine the position of the human torso.

Bending sensors 135 (see FIG. 1) discussed above are merely examples of myriad sensors that may be employed in the back brace apparatus 100. Other sensors are known to those of skill in the art and may be employed in other embodiments without departing from the invention. For example, some sensors are co-packaged and integrated such that one sensor may employ multiple sensing techniques that all work in conjunction with each other to indicate the change in position of the torso to the controller 145 (see FIG. 1). Further embodiments may employ external sensors such as those contained within cellular phones and other external devices. For example, a cellular phone may be secured to the human torso and the sensors within the phone may indicate the change in position of the human torso to the controller. The external device may provide input to the controller 145 (see FIG. 1) using wired or wireless communication, as described in more detail below.

Some embodiments may employ a single bending sensor 135 (see FIG. 1) while other embodiments may employ a plurality of bending sensors that may work in conjunction with one another to aid in the detection of a change event of a human torso. For example, one embodiment may employ a single bending sensor 135 (see FIG. 1) such as sensor 135a (see FIG. 8A). Another embodiment may employ bending sensor 135a (see FIG. 8A) in addition to multiple accelerometers, a gravity sensor and a plurality of pressure sensors. Embodiments that employ a plurality of sensors may have an algorithm that the controller 145 (see FIG. 1) uses to enable more accurate sensing of a change event of the human torso. For example, a single sensor such as the sensor 135a (see FIG. 8A) may not be able to differentiate between a bending event and the user distending their stomach. However, the bending sensor 135a (see FIG. 8A) in conjunction with other bending sensors may be able to use input such as the angle of the upper portion of the human torso 710 (see FIG. 7A), the change in pressure at different locations within the belt segments 105, 110 (see FIG. 1), and the acceleration of different portions of the belt segments to differentiate between a bending event and a distended stomach. In some embodiments the differentiation may be desirable to enable more accurate activation of the back brace adjustment system 120 (see FIG. 1) to protect the user.

For example, in one embodiment a deflectable bending sensor may be used in the front and on the back of the back brace apparatus. Input from the front and back sensors may be compared by the controller to more accurately determine if the user is bending, where both sensors should indicate a change event, or if the user is distending their stomach where only the front sensor should indicate a change event.

Figure 9:
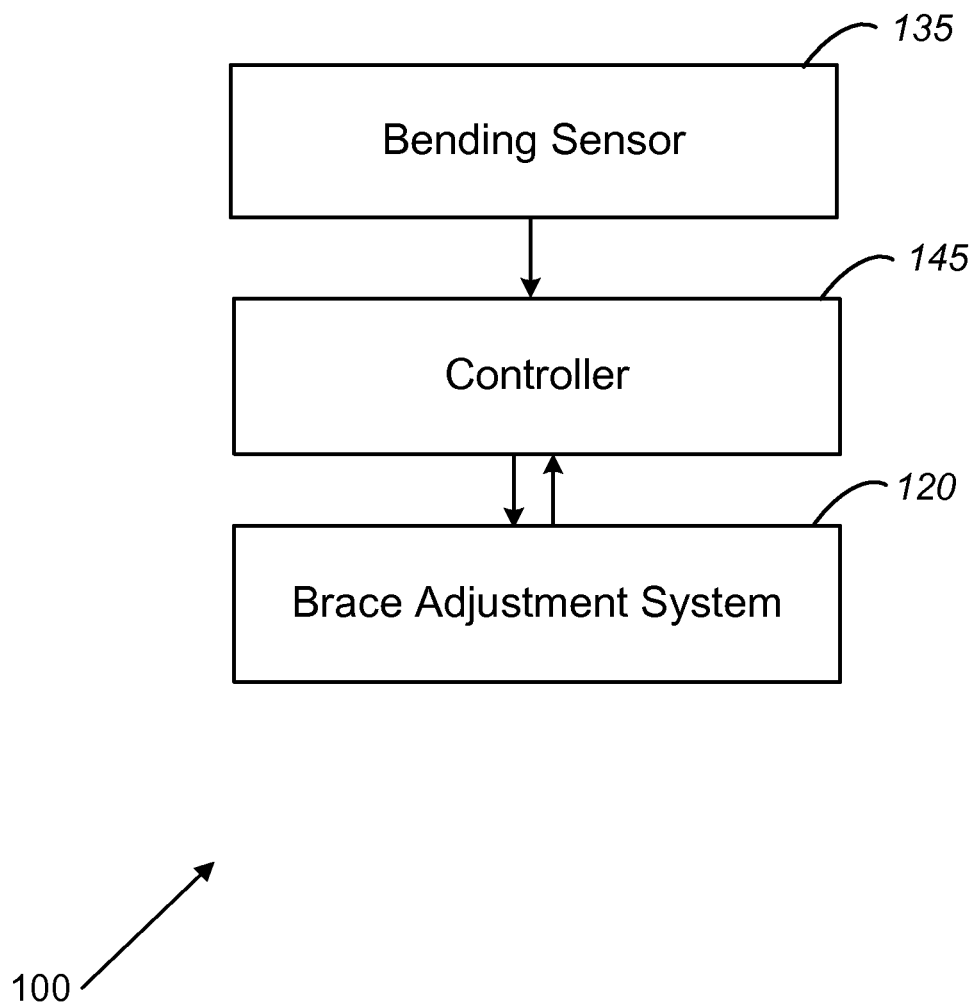
FIG. 9 is a block diagram that illustrates components of a back brace apparatus constructed in accordance with an embodiment of the invention.

A system diagram of one embodiment of the interconnection of the electronic components within the back brace apparatus 100 is illustrated in FIG. 9. The one or more bending sensors 135 may be connected to provide input to the controller 145. In some embodiments, the one or more bending sensors 135 may be continuously variable, while in other embodiments the sensors may detect only a bending position and a standing position. The controller 145 may use the input from the one or more bending sensors 135 to determine the appropriate state of the back brace. For example, if the bending sensors 135 detect a bending position, the controller 145 may communicate with the brace adjustment system 120 to increase the support to a back portion of a user's torso. Similarly, if the bending sensors 135 detect a standing position, the controller 145 may communicate with the brace adjustment system 120 to decrease the support to a back portion of a user's torso. In some embodiments, the brace adjustment system 120 may send the controller 145 feedback regarding the state of the back brace apparatus 100 (see FIG. 1). For example, if a servo motor is used in the brace adjustment system 120 (see FIG. 1) it may send an encoder position indicating the position of the cable tensioning device, or current feedback indicating the tension in the cable 160 to the controller 145. In other embodiments, other sensors such as a belt tension sensor may be located on the back brace apparatus and provide feedback to the controller 145 so the appropriate amount of tension may be placed on the belt segments 105, 110.

Figure 10:
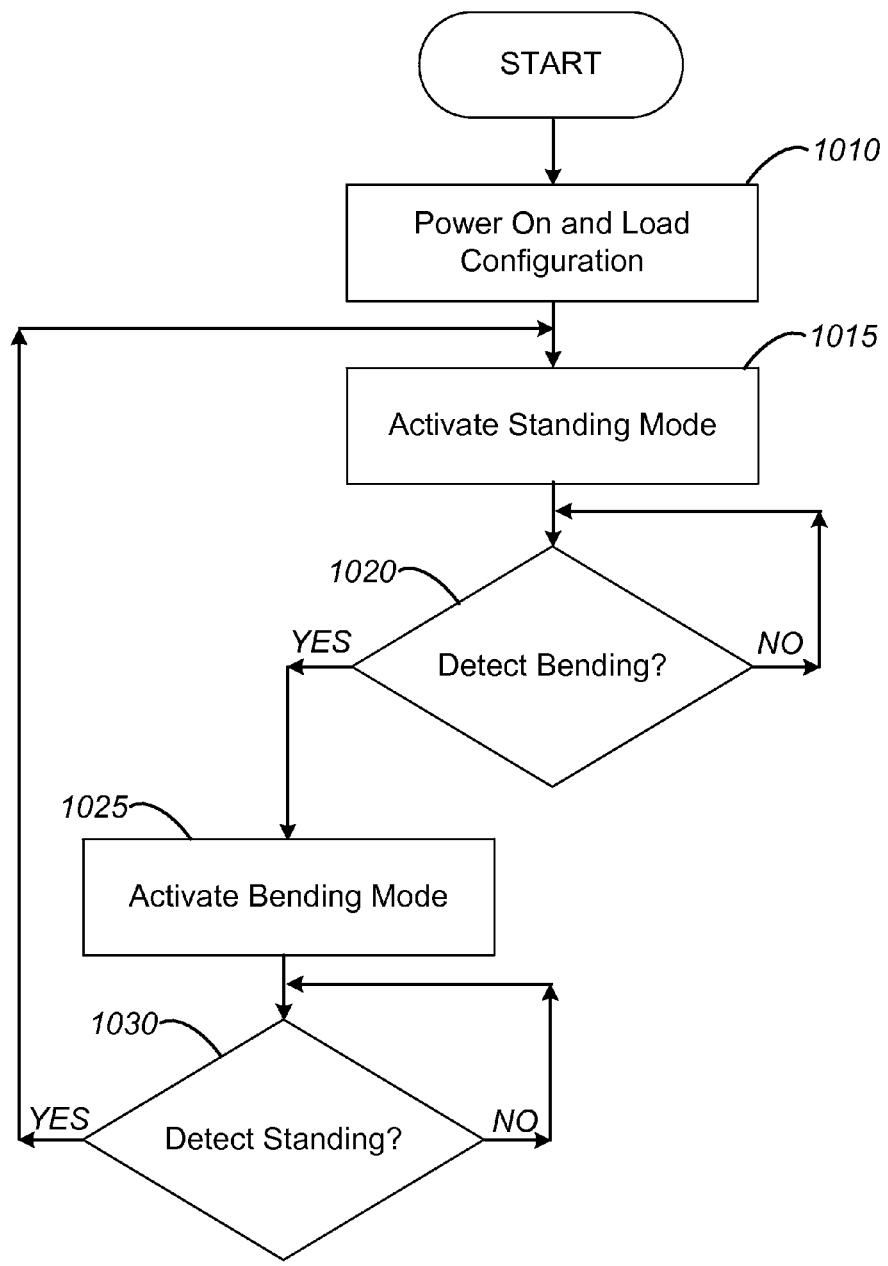
FIG. 10 is a flow diagram that illustrates operations of a controller of a back brace apparatus, in accordance with an embodiment of the invention.

In some embodiments, the controller may follow a logic structure 1000 as illustrated in FIG. 10. The illustrated operation begins at the flow diagram box numbered 1010 when the user may turn the power on to the back brace apparatus 100 to provide electrical energy to the controller and the controller 145 may load the appropriate configuration parameters from memory. In some embodiments, the controller 145 may be preprogrammed by a clinician who sets the appropriate parameters so the apparatus has the proper tension or support in the user standing position and in the user bending position. In other embodiments, the user may program the device and set the appropriate parameters. For example, such parameters may be the bending angle of the human torso that triggers the controller 145 to recognize a transition in position from a standing position to a bending position. Another parameter may be the appropriate amount of support the back brace adjustment system 120 is to provide to the back portion of the user's torso when transitioning to a bending position. Another parameter may be the bending angle of the human torso that triggers the controller to recognize a transition in position from a bending position to a standing position. An additional parameter may be the appropriate amount of support the back brace adjustment system 120 is to provide to the back portion of the user's torso when transitioning to a standing position. In some embodiments the back brace apparatus 100 may be programmed to apply the appropriate amount of support to the back portion of the user's torso when initially fit onto the torso and activated. Other parameters may be set and employed without departing from the invention. As a final operation, in some embodiments, the controller may check to determine that the back brace is secured to a user's torso, before activating the back brace adjustment system 120.

Next, at operation 1015, the parameters appropriate for the standing position may be acted upon by the controller 145. In some embodiments the back brace apparatus 100 may be in a fully relaxed configuration prior to being secured to the user's torso and activated. Once the back brace apparatus 100 is secured to the user's torso and active, the controller 145 may enter the standing mode wherein the back brace adjustment system 120 may change the state of the back brace to apply the appropriate amount of support to the back portion of the user's torso. As discussed above, myriad sensors may be employed to control the appropriate amount of support.

Next, at the decision box numbered 1020, the controller 145 may detect whether or not the human torso has experienced a change event by bending. If there is no bending detected, the controller 145 may take no action. However, if bending is detected, the controller 145 may move to the operation 1025.

In operation 1025 the controller 145 may activate the bending mode. In this operation the controller 145 may command the back brace adjustment system 120 to change the state of the back brace apparatus to the bending mode, for example by increasing the support to the back portion of the user's torso. As discussed above, myriad sensors may be employed to control the appropriate amount of support.

Next, the controller operation may move to the decision box 1030. Here, the controller 145 detects whether or not the human torso has experienced a change event by standing. If there is no standing detected, the controller may take no action. However, if standing is detected, the controller may move to the operation 1015.

In operation 1015 the standing mode may be re-activated. In this operation the controller may command the back brace adjustment system 120 to change the state of the back brace apparatus 100 to re-activate the standing mode, for example by decreasing the support to the back portion of the user's torso.

During operation, the controller 145 may employ input from myriad sensors or devices, other than only the bending sensors 135. For example, the controller may continuously monitor a separate tension or belt length gauge in the belt segments 105, 110 to determine if the back brace adjustment apparatus 100 is working properly. In the case that the back brace adjustment apparatus 100 accidentally provides too much support to a back portion of a human torso, for example by over tensioning the cable 160 (see FIG. 1), the controller 145 may use that input to trigger an emergency shutdown of the system.

Figure 11:
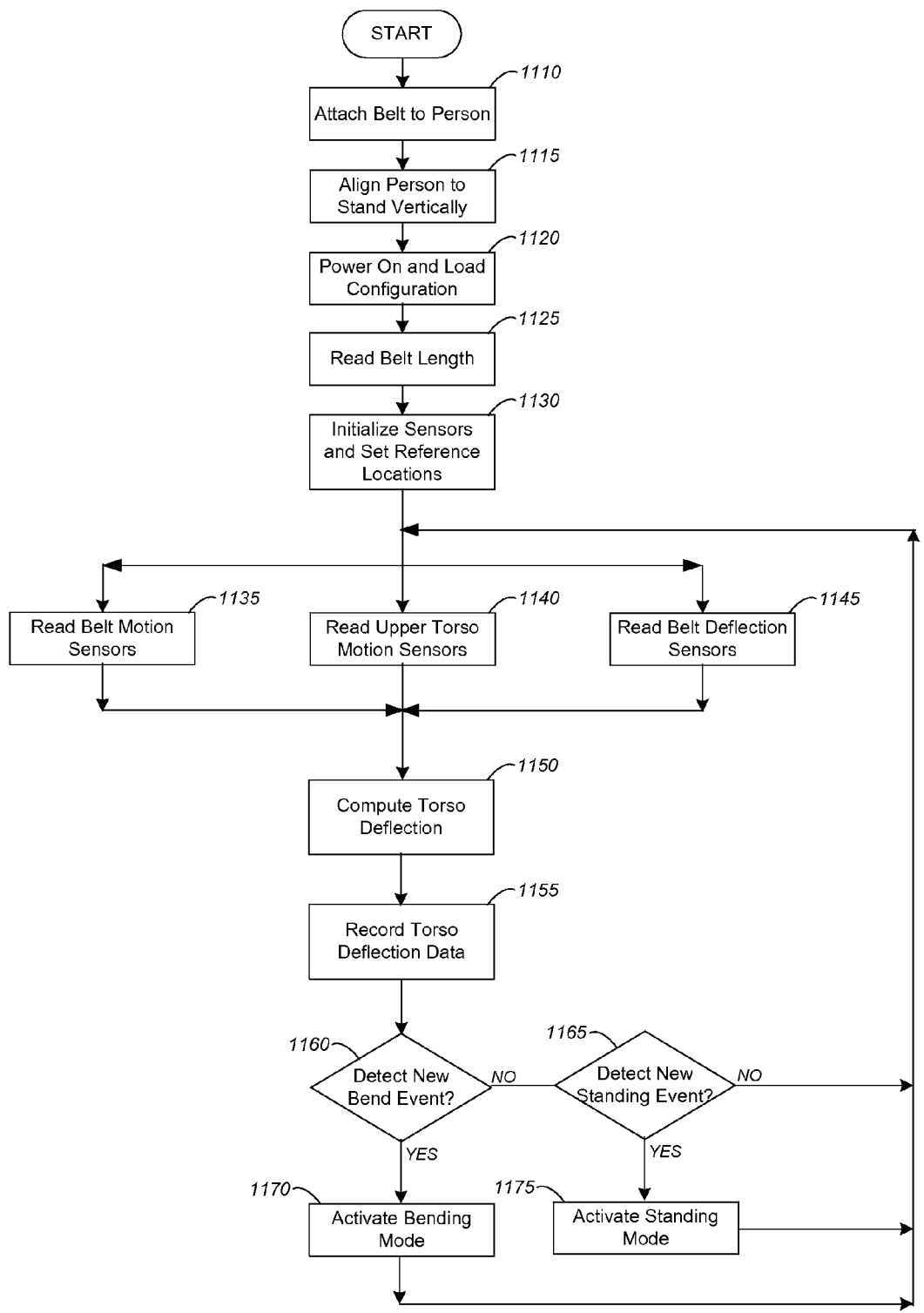
FIG. 11 is a method of using and operating a back brace apparatus in accordance with an embodiment of the invention.

In some embodiments, the controller may follow a logic structure 1100 as illustrated in FIG. 11. The illustrated operation begins at the flow diagram box numbered 1110 when the belt is attached to the person to be monitored. In some embodiments additional sensors other than those disposed in the belt may be attached to the person. In the operation 1115 the person may be aligned to stand vertically so the sensors may be calibrated to a known state of the person. In the operation 1120 an operator may turn the power on to the back brace apparatus to provide electrical energy to the controller and the controller may load the appropriate configuration parameters. In some embodiments, the controller may be preprogrammed by a clinician who sets the appropriate parameters so the apparatus has the proper tension or support in the user standing position and in the user bending position. In other embodiments, the user may program the device and set the appropriate parameters. For example, such parameters may include the bending angle of the human torso that triggers the controller to recognize a transition in position from a standing position to a bending position. In other embodiments the controller may be configured to a monitoring setting where the back brace apparatus may not tighten or loosen but may only monitor the user's movements (sensor apparatus) and record the data for later analysis by a clinician.

In the operation 1125, in some embodiments, belts that are configured with a belt length sensor may read the belt length to determine the approximate location of the sensors on the belt. In the operation 1130 the one or more sensors may be initialized and the reference locations set. More specifically, the starting reference position of all the sensors may be nulled so that any changes from the vertical standing position may be determined by the relative change in the sensors from the starting position. In some embodiments there may be a plurality of sensors arranged on coordinate axes as illustrated in FIG. 8E.

Next, multiple sensor readings may be performed in parallel, relatively simultaneously or sequentially. In the operation 1135, belt motion sensors are read. In some embodiments these are accelerometer/gyro sensors attached to one or more locations on the back brace apparatus. In the operation 1140 upper torso motion sensors may be read. In some embodiments these sensors may be attached to one or more locations on the user's upper torso and may be accelerometer or IMU sensors. In the operation 1145 belt deflection sensors may be read. In some embodiments these sensors may be deflection sensors, such as strain gauges, that read deflections in the belt and/or deflections in the user's body.

In the operation 1150, the torso deflection may be calculated from a combination of the sensors read in operations 1135, 1140 and 1145. In some embodiments the readings from the sensors may be used to accurately determine the deflection of the upper torso of the user. More specifically, in some embodiments, readings from sensors may be compared using one or more algorithms to extract accurate motion regarding the user's torso. Some sensors may be used to null out noise from other sensors. In the operation 1155, in some embodiments, torso deflection data may be recorded. Data may be recorded in an on-board memory disposed on the belt or the data may be wirelessly transferred to a remote storage device. The data may be used by a clinician to assess the user's motion while wearing the back brace apparatus. In some embodiments the recording operation may not be used.

In some embodiments, the back brace apparatus parameters appropriate for the standing position may be acted upon by the controller while the user is in the standing position. In some embodiments the back brace apparatus may be in a fully relaxed configuration prior to being secured to the user's torso and activated. Once the back brace apparatus is secured to the user's torso and active, the controller may enter a standing mode wherein the back brace adjustment system may change the state of the back brace to apply the appropriate amount of support to the back portion of the user's torso. As discussed above, myriad sensors may be employed to control the appropriate amount of support.

Next, at the decision operation numbered 1160, the controller may detect, using the computed torso deflection, whether or not the human torso has experienced a new bending event. In some embodiments threshold parameters may be set by a clinician to determine if a new bending event has occurred. If there is no new bending event detected, the controller may advance to the decision operation 1165 to determine if a standing event has occurred. However, if a new bending event has been detected, the controller may move to the operation 1170 to activate a bending mode. A new bending event is a bending event that has not been previously detected by the controller.

In the operation 1170 the controller may activate the bending mode. In this operation the controller may command the back brace adjustment system to change the state of the back brace apparatus, for example by increasing the support to the back portion of the user's torso. As discussed above, myriad sensors may be employed to control the appropriate amount of support. After the back brace applies the appropriate amount of support the program may return to the operations 1135, 1140 and 1145 to read the plurality of sensors.

In the decision operation 1165, the controller may determine if a new standing event has occurred. If no new standing event has occurred, the controller proceeds back to operations 1135, 1140 and 1145 to read the sensors. In some embodiments a standing event may be determined by the clinician setting a threshold parameter. If a new standing event has occurred, the controller proceeds to the operation 1175. If no new standing event has occurred, the controller may proceed back to the operations 1135, 1140 and 1145 to read the sensors. A new standing event is a standing event that has not been previously detected by the controller.

In the operation 1175 a standing mode may be activated by the controller. In this operation the controller may command the back brace adjustment system to change the state of the back brace apparatus, for example by decreasing the support to the back portion of the user's torso. After the state of the back brace has been changed the controller may proceed back to operations 1135, 1140 and 1145 to read the sensors.

During operation, the controller may employ input from myriad sensors or devices, other than only bending sensors read in the operations 1135, 1140 and 1145. For example, the controller may continuously monitor a separate tension gauge in the belt segments to determine if the back brace adjustment apparatus is working properly. In the case that the back brace adjustment apparatus 100 accidentally provides too much support to a back portion of a human torso, for example by over tensioning cable 160 (see FIG. 1), the controller may use that input to trigger an emergency shutdown of the system. In further embodiments other emergency release mechanisms may be used such as a separate button or a mechanical release.

In some embodiments the back brace apparatus may be configured to be completely passive where there is no tensioning device and the back brace apparatus simply collects data on the user's back deflection (torso movements). Such an embodiment may be described as a sensor apparatus and used by a clinician to assess the user's back movements during their daily routines to monitor the effects on their back. The data may then be used to select an appropriate treatment program including the use of a back brace apparatus with an integrated tensioning device as described herein. In some embodiments, for example, the sensor apparatus may have one or more of a micro-controller, one or more sensors and a battery integrated into the belt. In further embodiments the sensor apparatus may be worn in conjunction with a belt having a tensioning device. More specifically, in some embodiments a sensor apparatus belt and a tensioning belt may be separate belts, but worn together. In one embodiment a sensor apparatus belt may be worn independently while in another embodiment a sensor apparatus belt may be worn in combination with a tensioning belt. The two belts may communicate via a wired or a wireless protocol and interact similarly as an integrated belt (i.e., belts having at least a tensioning device, sensors and a controller), as described herein.

Figure 12:
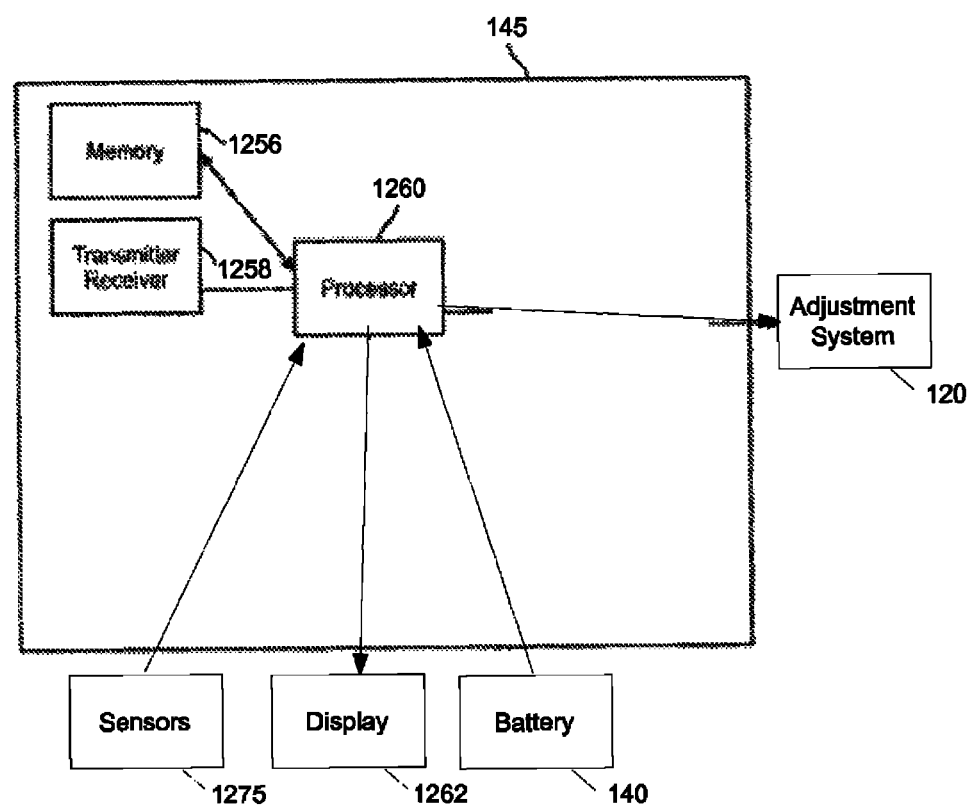
FIG. 12 is a system diagram of a back brace apparatus in accordance with an embodiment of the invention.

As shown in FIG. 12, the back brace apparatus controller 145 may have a processor 1260 that functions to control the overall operation of the device. Processor 1260 may include programming that functions to control the respective device and its components. Processor 1260 may communicate with and/or control the back brace adjustment system 120, output/display 1262 (if equipped), memory 1256, sensors 1275, transmitter/receiver 1258 and the like. The processor of the back brace apparatus 100 (see FIG. 1) may communicate with the processor of other electronic devices, for example, through the transmitter/receiver 1258. As mentioned above, the processor may employ sensor input from external devices such as a cell phone. The processor may include programming that can be executed to control the back brace adjustment system 120, the data to be displayed by the display (if equipped), the battery 140, the data to be transmitted via the transmitter, etc.

The controller 145 may include a memory device 1256. The memory device 1256 may be any type of memory capable of storing data and communicating that data to one or more other components of the device, such as the processor. The memory device may be one or more of a Flash memory, SD card, SRAM, ROM, DRAM, RAM, EPROM, dynamic storage, and the like.

The processor 1260 and/or memory device 1256 may also include programming that allows the processor to receive signals and/or other data from an input device, such as one or more sensors that sense gravity, acceleration, strain, change in position, and the like, that may be included as a part of the device or used in conjunction therewith. The processor 1260 may receive data, for instance, from a transmitter/receiver on a cellular phone and store the data in the memory device 1256.

The processor 1260 may also include additional programming to allow the processor to learn user preferences and/or user characteristics and/or user history data, for instance, to implement changes in use suggestions based on detected trends, such as bending position or standing position trigger points, bending or standing position back brace support settings, settings for different users, settings for different tasks; and may include programming that allows the device to generate reports, such as reports based upon user history, compliance, trending, and/or other such data. Additionally, some embodiments may include a "power off" or "suspend" function for suspending one or more functions of the device, such as suspending a change in state of the back brace apparatus 100 (see FIG. 1), and/or for powering off the device or deactivating the back brace adjustment system. In some embodiments, one or all of the functions of processor 1260 described herein may be performed by an external processor.

The back brace apparatus 100 (see FIG. 1) may include a power charging mechanism (not shown) in some cases, such as a USB port, induction charger, or the like. The power charging system may be used to charge a battery 140 that may be a power storage cell such as a rechargeable battery. Some embodiments may use a rechargeable battery 140 such as a NiCad battery, LiPo battery, NiMH battery or the like. In some embodiments, the power charging mechanism may be a USB port or charging system connected to a standardized wall outlet. As such, all data may be kept in the controller 145 for easy downloading of data to a computer using the USB port. The USB port may also provide the battery 140 with power charging. In some embodiments, the power charging mechanism may be an induction charging device.

It will be appreciated that the back brace apparatus and sensor apparatus described herein are illustrative and that variations and modifications are possible. For instance, the apparatuses may employ one or more adaptations to increase comfort and/or effectiveness. For example, the apparatuses may have portions comprising a gel, a viscoelastic material, cushioning or foam. In addition, one or more coverings may be employed on all or portions of the apparatus such as nylon, cotton, silk or felt.

In the description, various embodiments have been described. For purposes of explanation, specific configurations and details are set forth in order to provide a thorough understanding of the embodiments. It will also be apparent to one skilled in the art that the present invention can be practiced without the specific details described herein. Furthermore, well-known features may be omitted or simplified in order not to obscure the embodiment being described.

Certain embodiments of the present invention relate to automated back braces that may employ one or more bending sensors. While the present invention can be useful to produce back braces for a wide variety of uses, some embodiments of the invention are particularly useful for producing back braces for applications that require automatic adjustment, as described in more detail herein.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A back brace apparatus fittable to a human torso, the back brace apparatus comprising:
    a belt configured to be worn around a waist of the human torso;
    a bending sensor comprising an elongated tab disposed on a front portion of the belt and adapted to be vertically aligned with the human torso and configured to detect a change event of the human torso by being deflected by a stomach portion of the torso;
    a back brace adjustment system capable of changing a state of the back brace apparatus between a tensioned state when the torso is in a bending position and a relaxed state when the torso is in a standing position; and
    a controller configured to control the back brace adjustment system to change the state of the back brace apparatus in response the sensor detecting the change event;
    wherein the elongated tab is formed in a U-shape having a first portion disposed on an interior surface of the front portion of the belt, a second portion disposed on an exterior surface of the front portion of the belt and a U-shaped portion formed over a top edge of the belt connecting the first portion and the second portion.

2. The back brace apparatus set forth in claim 1 wherein the back brace adjustment system includes a cable and pulley mechanism coupled to a tensioning device.

3. The back brace apparatus set forth in claim 1 wherein the sensor is configured to detect an angle of an upper portion of the human torso relative to a lower portion of the human torso.

4. The back brace apparatus set forth in claim 1 wherein the sensor comprises a strain gauge.

5. The back brace apparatus set forth in claim 1 wherein the sensor comprises a potentiometer.

* * * * *